United States Patent [19]

Kubota et al.

[11] 3,996,792

[45] Dec. 14, 1976

[54] SUPERSONIC WAVE FLAW DETECTING APPARATUS

[75] Inventors: Jun Kubota; Soji Sasaki, both of Hitachi, Japan

[73] Assignee: Hitachi, Ltd., Japan

[22] Filed: July 1, 1975

[21] Appl. No.: 592,359

[30] Foreign Application Priority Data

July 3, 1974 Japan .................. 49-75313

[52] U.S. Cl. .................................. 73/67.8 S
[51] Int. Cl.[2] ................................. G01N 29/04
[58] Field of Search ........... 73/67.8 R, 67.8 S, 67.9

[56] References Cited
UNITED STATES PATENTS

| | | | |
|---|---|---|---|
| 3,023,611 | 3/1962 | Howry | 73/67.8 S |
| 3,086,390 | 4/1963 | Brown | 73/67.8 S |
| 3,308,652 | 3/1967 | Appel et al. | 73/67.8 S X |
| 3,924,452 | 12/1975 | Meyer et al. | 73/67.8 S |

*Primary Examiner*—Richard C. Queisser
*Assistant Examiner*—John P. Beauchamp
*Attorney, Agent, or Firm*—Craig & Antonelli

[57] ABSTRACT

A supersonic or ultrasonic wave flaw detector in which acoustic boundaries of flaws and/or abnormality of materials within an object to be inspected is detected by supersonic or ultrasonic waves and the position and shape of such a flaw and/or abnormality are displayed. A hard object to be inspected is sector-scanned with a supersonic wave beam with a variable-angle beam probe in direct contact with the object. In a range of comparatively small incident angles at which the longitudinal wave mainly penetrates the object, sectional images due to echo signals of the longitudinal wave are displayed on a display screen with scanning lines representative of the transmission speed and direction of the longitudinal wave. In the range of large incident angles where the shear wave penetrates the object, on the other hand, sectional images due to the echo signals of the shear wave are displayed on the display screen with scanning lines representative of the transmission speed and direction of the shear wave. For this, the sweeping speed and direction for the display scanning lines are switched in accordance with the ranges of incident angles. The switched flaw detecting operation modes of longitudinal and shear waves thus combined covers a complete sectional image to be displayed on the display screen.

13 Claims, 16 Drawing Figures

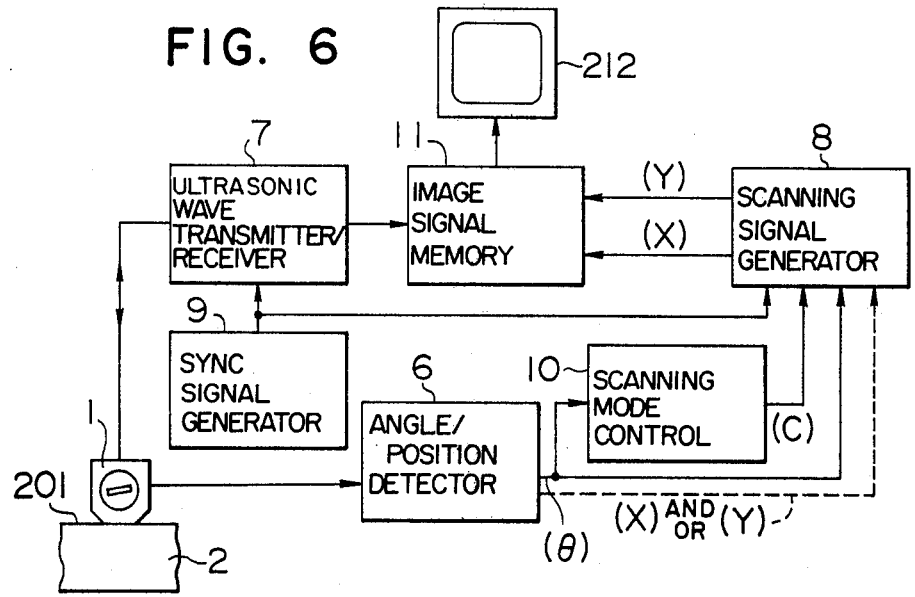
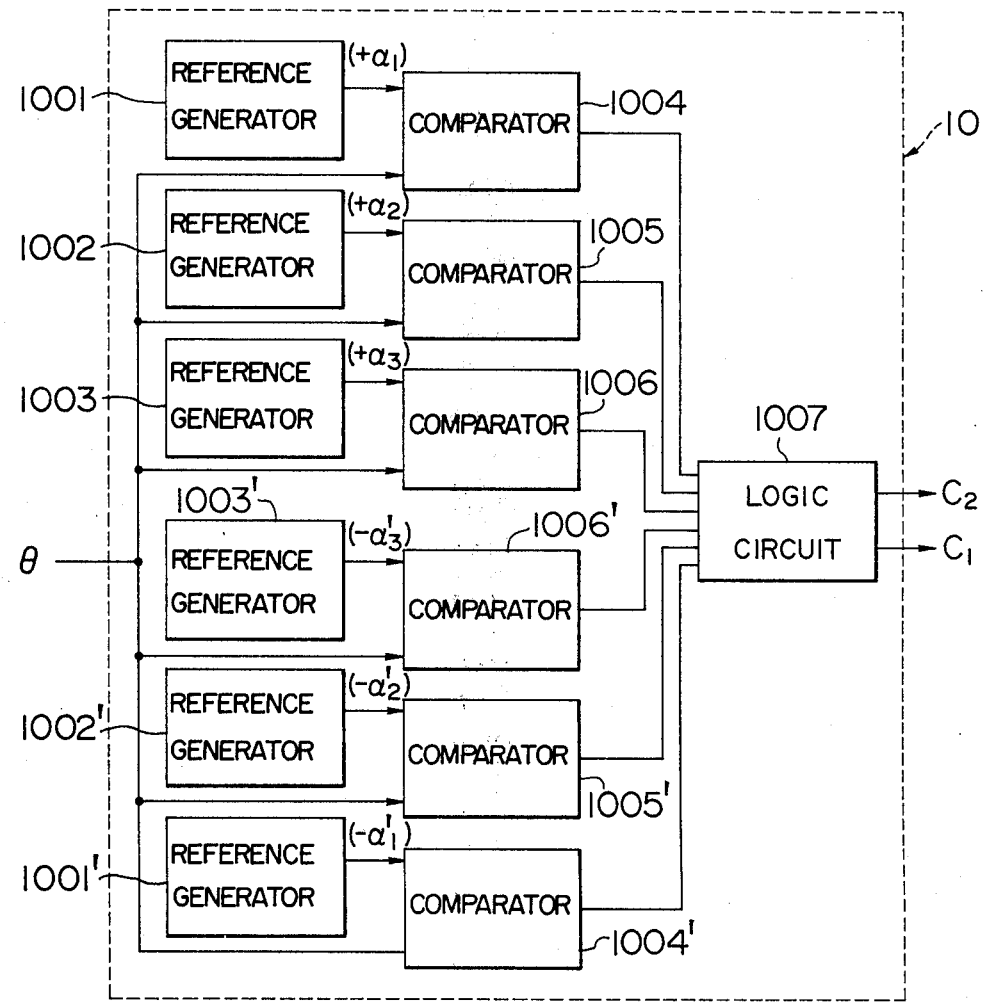

SUPERSONIC WAVE FLAW DETECTING APPARATUS

BACKGROUND OF THE INVENTION

1. Field of the Invention

This invention relates to a supersonic or ultrasonic wave flaw detecting apparatus for detecting acoustic boundaries of flaws and/or abnormal parts of materials within an object to be inspected, by the use of supersonic or ultrasonic waves and for displaying the position and shape of the flaws or abnormality.

2. Description of the Prior Art

A well-known method for detecting a flaw and the like within an object by the use of supersonic waves includes what is called the pulse echo method. In this method, supersonic wave pulses are made to penetrate the object to be inspected and the absence or presence of a flaw is determined by receipt of an echo signal reflected and returned from the inside of the object.

It is also well known that the most widely used method for displaying the signal derived in the pulse echo method is the A scope method in which the chronological changes in signal intensity, namely, a signal waveform is displayed. The A scope method, however, has the disadvantage that it is often difficult to determine at which points within the object the many echo signals displayed on the display screen of the cathode ray tube are reflected. This is especially difficult when a complicated shape of the object is involved.

Beside the above-mentioned A scope method having such a disadvantage, there is what is called the B scope method. In this method, the scanning lines on CRT is brightness-modulated by the echo signals and displayed in synchronism with the movement of penetration path of the supersonic wave beam thereby to produce a sectional image of the object. The advantage of this method is that the image due to the echo signals based on the presence of a flaw or abnormality of material represents the relative position of the abnormality within the section of the object as well as the shape thereof, thus greatly facilitating the checking of the inspection results.

When the object to be inspected is made up of a living body, its internal organ or frame-work forms acoustic boundaries. In the event that the boundary surfaces within the object on which supersonic waves are reflected are in various directions, what is called the compound scanning system is employed. In this method, the scanning by sectorially changing the direction of the path of the incident supersonic wave beam is combined with the scanning by moving the point of transmission and receipt of the wave, namely, the position of the probe. The scanning lines on the display section comprising a CRT is relocated in synchronism with the path of the supersonic wave beam which is changing at every moment. The scanning lines are brightness-modulated by echo signals received, thereby displaying the state of a sectional area of the object to be inspected.

Specifically, the sector scanning according to the compound scanning system employs two different methods. One of them is the water immersion method, in which the direction of the probe is capable of being changed freely by using such a liquid as water as a transmission medium for supersonic waves. The other method is one used for an object such as a living body having soft boundary surfaces, in which the direction of the probe, namely, the direction of transmission of the supersonic wave beam is changed while maintaining the probe in direct contact with the object to be inspected.

The last-mentioned direct-contact method cannot be used when the object to be inspected is made of metal or other hard material and in addition has a sound speed different from that in the transmission medium of the supersonic wave.

In the case of the water immersion method using water or the like as a contact medium, the transmission path of the supersonic wave beam is refracted at the plane of incidence of wave at the surface of the object of inspection. Therefore, it is necessary to refract the scanning lines for indication of images on the B scope in accordance with the transmission path. In the event that the length of the transmission path of the supersonic wave in a liquid from the transmission point of the supersonic wave pulses to the point of incidence into the object of inspection undergoes variations, it is quite difficult and requires very high skill to refract the scanning line in the above-mentioned manner.

The display scanning lines on the screen of the conventional display apparatus is generated by the sweep in accordance with the speed and direction of transmission of supersonic wave in the object of inspection. In such a conventional apparatus, the speed and direction of sweep is determined on the basis of only one of the two modes; one is a longitudinal wave (in which the direction of displacement of the transmission medium coincides with the direction of propagation of the wave) and the other is a shear wave (in which the direction of displacement of transmission medium is perpendicular to the direction of propagation of the wave). In the case where the incident angle of the supersonic wave is in the vicinity of zero, namely, in the case where the supersonic wave enters the object at substantially right angles to the surface thereof, the supersonic wave penetrating the object mainly follows the mode of longitudinal wave. Accordingly as the incident angle is increased so that the supersonic wave enters the object obliquely, however, the influence of the shear wave is gradually increased, and the modes of both longitudinal and shear waves come to coexist in the object of inspection. As a result, with the increase in the incident angle, the shear wave mode undesirably exists in addition to the required longitudinal wave mode. Thus a useless and harmful image as well as the image of a section of the object originally intended for is displayed. This often leads to an error in examination of the results of supersonic wave flaw-detecting operation and forms a roadblock to successful flaw detection.

With further increase in incident angle, the efficiency of incidence of the longitudinal wave into the object is sharply decreased, thus posing another problem of reduced sensitivity of flaw detection by the longitudinal wave.

SUMMARY OF THE INVENTION

Accordingly, the present invention is intended to obviate the disadvantage of the conventional methods of supersonic wave flaw detection in which the scanning and display of a sectional view of the inspection object on the basis of merely one of the modes of longitudinal and shear waves has a limit of the practical range of flaw detection and an undesirable signal comes to coexist.

An object of the invention is to provide a supersonic wave flaw detecting apparatus of a sector scanning type which is capable of maintaining a high flaw detecting sensitivity over the whole range from 0° to 90° of the refraction angle of the supersonic wave in an inspection object.

In order to achieve the above-mentioned object, the present invention is characterized in that the display scanning lines on the display screen are associated with the speed and direction of the transmission of longitudinal waves in a range of comparatively small incident angles while the display scanning lines on the display screen are associated with the speed and direction of transmission of shear waves in the range of comparatively large incident angles where the shear wave mode is predominant in the inspection object. The speed and direction of sweep are switched in accordance with the ranges. The modes of both longitudinal and shear waves are used in combination and displayed as one sectional image on the display screen.

BRIEF DESCRIPTION OF THE DRAWINGS

FIG. 6 is a block diagram showing a supersonic wave flaw detecting apparatus of a sector scanning type according to an embodiment of the invention.

FIG. 7a is a block diagram showing an example of configuration of the scanning mode control section included in the apparatus shown in FIG. 6.

FIG. 7b is a diagram showing another embodiment of the section shown in FIG. 7a.

DETAILED DESCRIPTION OF THE PREFERRED EMBODIMENTS

Figure 1:
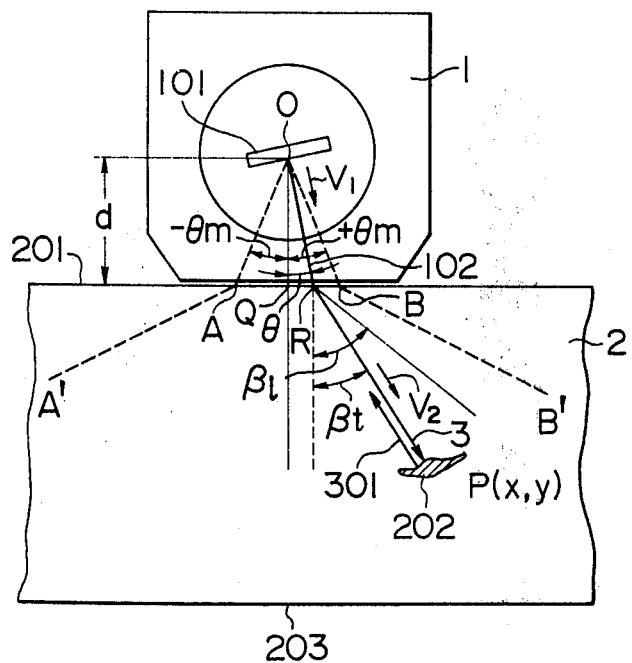
FIG. 1 is a diagram for explaining the operation of the variable-angle beam probe of a sector scanning type used with the apparatus according to the present invention.
Figure 2:
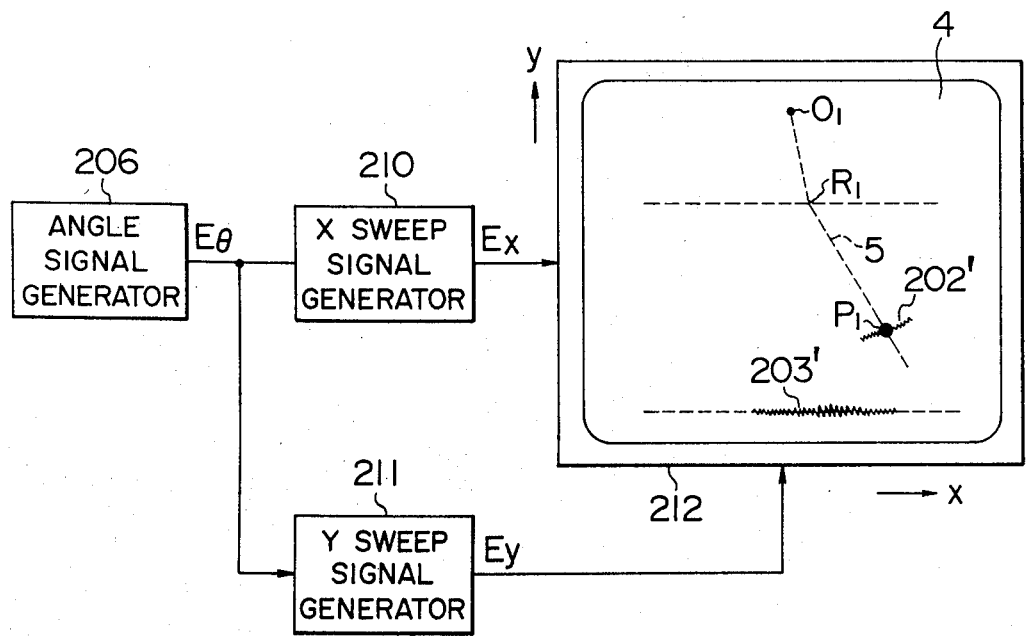
FIG. 2 is a diagram for explaining the method of displaying a section by the sector scanning.

Referring to FIG. 1 showing a diagram for explaining the operation of the variable angle beam probe of a sector scanning type, reference numeral 1 shows a variable angle beam probe having a supersonic wave transducer 101 capable of emitting and receiving supersonic waves, and numeral 2 an object to be inspected. The transducer 101 is arranged so that the direction of emission of supersonic waves are variable. The incident angle $\theta$ of the supersonic wave beam into the inspection object 2 is continuously changed by the use of the variable angle beam probe 1. Numeral 3 shows a supersonic wave beam penetrating the inspection object 2. The direction of emission of the supersonic wave beam 3 is swept in the sectional area between the directions AA' and BB' while receiving the echo 301. Distributed images 202' and 203' of the echo signals representing the acoustic boundaries in the object 2 such as a flaw 202 and a profile 203 are displayed on the display screen 4 of a displaying device 212 as shown in FIG. 2. According to this technique for detecting flaws by supersonic waves, the internal state of the object 2 is capable of being observed directly as a sectional image, and therefore it is easy to identify the position, direction and shape of the flaw in the object 2. Also, a wide area of the internal portions of the object 2 can be searched for flaws only by locating the variable angle beam probe 1 at a specified position on the surface of the inspection object 2, thus leading to the great advantage of an improved efficiency for flaw detecting operation.

Figure 5:
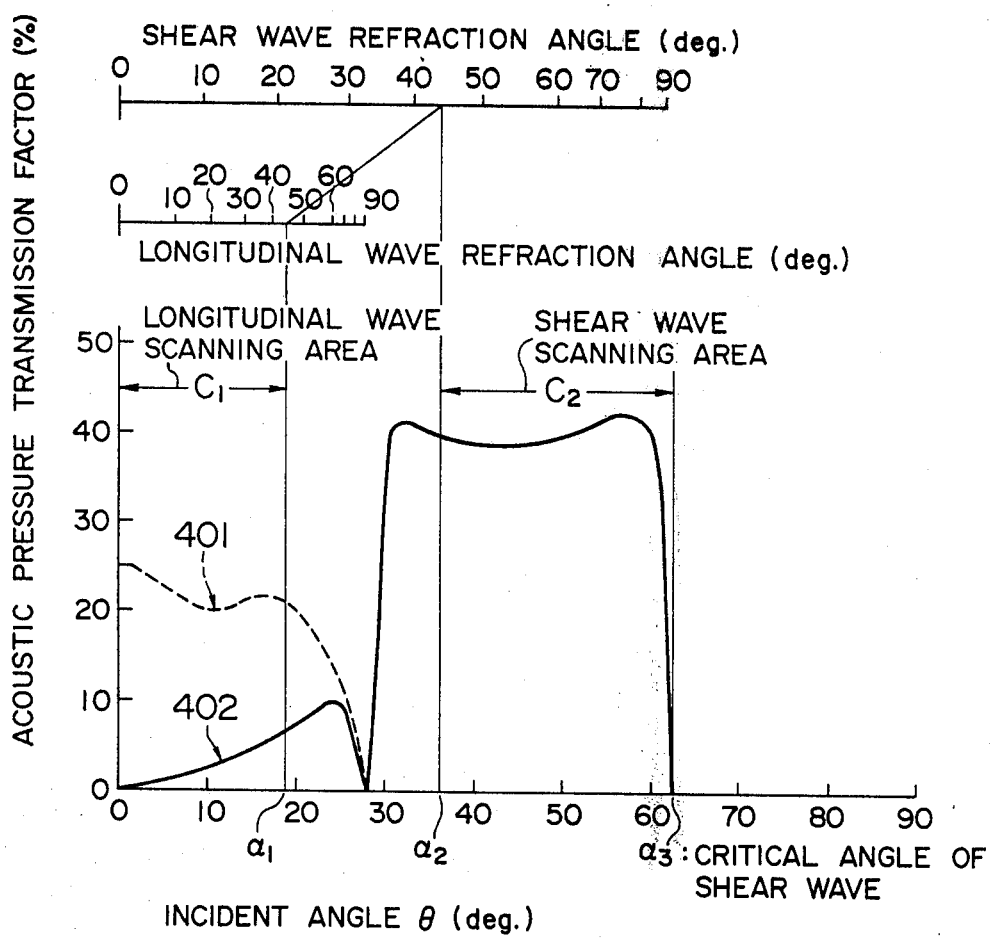
FIG. 5 is a diagram showing the relation between the efficiency of incident energy of the longitudinal and shear waves as against the angle of incidence of a supersonic wave beam into a rigid or hard object.

Assume, in performing sector scanning by a supersonic wave beam, that a supersonic wave transmission path 102 in the variable angle beam probe 1 is made of an organic glass, while the material of the object 2 is rigid such as steel in which the longitudinal wave sound velocity is 5850 m/sec and the sheer wave sound velocity is 3230 m/sec. The acoustic pressure transmission factor $$\left( \frac{\text{refraction angle energy}}{\text{incident angle energy}} \times 100 \text{ (\%)} \right)$$

of the supersonic wave entering the inspection object 2 from the variable angle beam probe (made of acrylic resin where the sound velocity is 2720 m/sec) depends on the mode of the supersonic wave, namely, on whether it is a longitudinal wave or shear wave. The acoustic pressure transmission factor thus undergoes changes against the incident angle $\theta$ as shown in FIG. 5. In the drawing under consideration, the curves 401 and 402 represent the cases involving longitudinal and shear waves respectively.

While the display scanning lines on the display screen 4 of the recording device are associated with the shear wave mode, the acoustic pressure transmission factor of the shear wave is low in the range of the supersonic wave incident angle $\theta$ from 0° to 28° which is the critical angle of the longitudinal wave. In this range, the influence of the longitudinal wave is so strong that the flaw detection by the shear wave is not practically reasonable. In spite of this, the shear wave mode coexists with the longitudinal wave mode from 19° to 28° of the incident angle. In the range of incident angle 30° or higher, the influence of the longitudinal wave is absent as it is totally reflected, while only the shear wave mode efficiently penetrates the object of inspection 2. Therefore, the last-mentioned range of incident angle is the most suitable for flaw detection by the shear wave. By the way, the incident angle 19° ($\alpha_1$ in FIG. 5) corresponds to the refraction angle of 45° of the longitudinal wave, and the refraction angle of 45° of the shear wave corresponds to the incident angle 36° (as shown by $\alpha_2$ in the drawing), the critical angle 62° of the shear wave being shown by $\alpha_3$.

In FIG. 1, suppose the transducer or oscillator element 101 for transmitting and receiving supersonic waves is disposed at angle $\theta$ with the normal OQ to the plane 201 of the object, that supersonic wave pulses are emitted at time $t = 0$ from the position 0 ($x = 0, y = 0$) of the transducer, that the supersonic wave is refracted at incident point R into the longitudinal wave $\beta_l$ and shear wave $\beta_t$, and that the shear wave $\beta_t$ has reached the point P by way of incident point R after time $t_P$.

The coordinates of the point P are $$x = d \cdot \tan \theta + V_2 \sin\phi \cdot (t_P - t_R) \qquad (1)$$

$$y = d + V_2 \cos\phi \cdot (t_P - t_R) \qquad (2)$$

where $$t_R = \frac{d}{V_1 \cos \theta}$$

Let the sound velocity in the medium from the transducer 101 to the surface 201 of the inspection object be $V_1$, and the velocity of the shear wave in the object 2 be $V_2$. And from Snell's law, the refraction angle $\phi$ of the supersonic wave beam at the incident plane of the object 2 is expressed as $$\sin \phi = \frac{V_2}{V_1} \sin \theta$$

From equations (1) and (2), $$x = d \cdot \tan \theta + \frac{V_2^2}{V_1} \cdot \sin \theta (t - t_R) \qquad (3)$$

$$y = d + V_2 \sqrt{1 - \left(\frac{V_2}{V_1}\right)^2 \sin^2 \theta} \, (t - t_R) \qquad (4)$$

If the refraction factor $$n \left(= \frac{V_2}{V_1}\right)$$

is used, they are rewritten as $$x = d \cdot \tan \theta + n \cdot V_2 \sin \theta (t - t_R) \qquad 5$$

$$y = d + V_2 \sqrt{1 - n^2 \sin^2 \theta} \, (t - t_R) \qquad 6$$

The values $d$ and $V_1$ depend on the size of the variable angle beam probe equipped with the transducer 1 and the material thereof, while the value $V_2$ is fixed by the material of the inspection object.

Reference is had to the block diagram of FIG. 2 showing the device for displaying the scanning lines. If an electrical signal $E_\theta$ corresponding to the incident angle $\theta$ is obtained, X and Y sweep signals for displaying the scanning lines on the display screen in accordance with the transmission path ORP of the supersonic wave beam are capable of being produced by constructing an X sweep signal generator 210 and a Y sweep signal generator 211. The output signals $E_x$ and $E_y$ from the generators 210, 211 are applied to the displaying device 212 of the CRT of B scope as X-axis and Y-axis deflection inputs, so that the scanning lines $O_1$-$R_1$-$P_1$ corresponding to the supersonic wave transmission path ORP are displayed. In the presence of a flaw, an image such as shown by 202' is displayed, the numeral 203' showing an image of the bottom of the inspection object. It is well known as what is called the B scope process that by brightness-modulating the scanning line by means of the echo signal derived from the inside of the object, a sectional image representing the shape of the acoustic boundary is displayed.

In this case, however, the fact must be taken into consideration that the return time of the echo signal corresponds to the time required for the supersonic wave to cover both ways along the path ORP. Then assuming that point O is expressed as ($x_0, y_0$) and the signal corresponding to ($x_0, y_0$) is obtained from position detector means not shown in the drawing, it is necessary to establish the correlation as described below between the sweep signals $E_x$ and $E_y$ by the amendment of equations (5) and (6).

$$E_x = x_0 + d \cdot \tan \theta + n \cdot \frac{V_2}{2} \sin \theta \, (t - t'_R) \qquad (7)$$

$$E_y = y_0 + d + \frac{V_2}{2} \sqrt{1 - n^2 \cdot \sin^2 \theta} \, (t - t'_R) \qquad (8)$$

where $t'_R$ to $2t_R$.

Figure 3A:
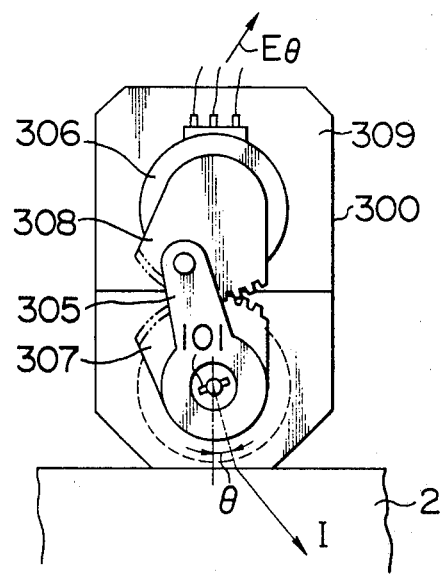
FIGS. 3a and 3b are diagrams showing a probe which may be used in the invention, in which 3a is a front view thereof and 3b a side view thereof.
Figure 3B:
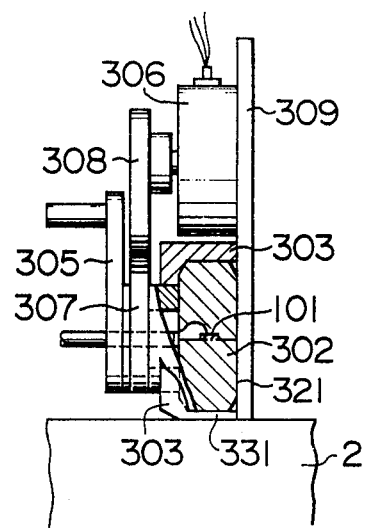

An example of the construction of a supersonic wave beam probe used in embodying the present invention will be explained below with reference to FIGS. 3a and 3b.

Reference numeral 101 shows a transducer for transmitting and receiving supersonic wave pulses, and numeral 302 a movable shoe acoustically coupled with the transducer element 101. The movable element 302 is made of a material which conducts supersonic waves well, and capable of sectorial movement reciprocally or rotation around the center axis A. Numeral 303 shows a holding shoe holding the movable shoe 302 and transmitting the supersonic waves to the inspection object 2 by way of the contact surface 331 between the slide face 321 and the object 2. Water, oil, glycerine or other similar contact medium in liquid form is applied to the slide face 321 and the contact surface 331 thereby to maintain the acoustic contact of the same, thus improving the transmission of the supersonic wave. Numeral 305 shows an operating lever for driving the movable shoe 302 into movement around the center axis A. The reciprocal/rotational movement resulting from the operation of the operating lever changes the angle $\theta$ at which the supersonic wave beam I sent out of the transducer 101 enters the object 2 by way of the movable shoe 302 and the holding shoe 303. The lever 305 may alternatively be operated automatically by utilizing a motor or other mechanical means. Numeral 306 shows a potentiometer for generating an electrical signal $E_\theta$ corresponding to the angle $\theta$ of sectorial motion of the movable shoe 302. The sectorial/reciprocal motion of the movable shoe 302 is transmitted through the gears 307 and 308. Numeral 309 shows a base plate on which the variable angle beam probe comprising the movable shoe 302 and the holding shoe 303 and the potentiometer 306 are mounted.

By means of the above-mentioned variable angle beam probe, it is possible not only to transmit and receive the supersonic wave in desired direction in the variable range of angle $\theta$ between $-\theta_m$ and $+\theta_m$ but to produce an electrical signal corresponding to the direction of the transmission and receiving.

Figure 4:
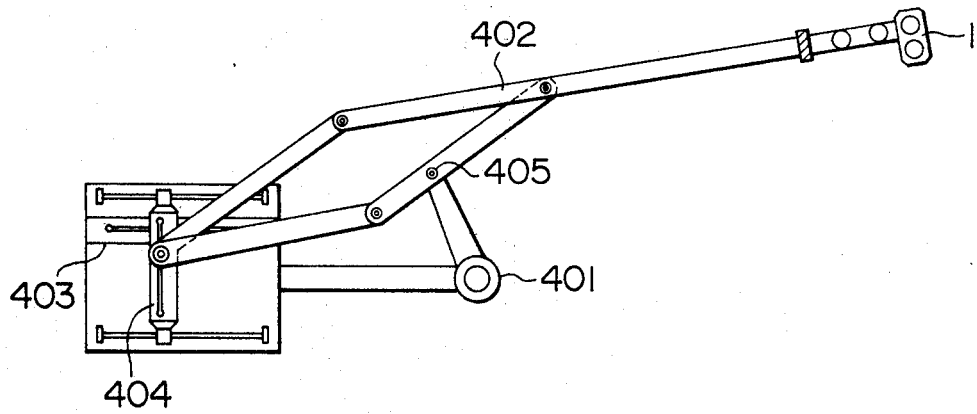
FIG. 4 a diagram showing a horizontal and vertical shaft device for the probe used with the apparatus of the present invention.

Reference is had to FIG. 4 showing a device for detecting the horizontal and vertical displacement of the variable angle beam probe.

The variable angle beam probe may be moved on the surface of the object in direct contact therewith either manually or automatically. If the transfer or shift scanning of the supersonic wave beam delivered from the variable angle beam probe is superimposed on the sector scanning thereof, a compound scanning is possible. The display of a sectional area by the supersonic wave using the compound scanning is also included in the scope of the present invention.

In FIG. 4, reference numeral 401 shows a support fixed at a desired point by a method not shown in the drawing. Numeral 402 shows a pantograph for transmitting the amount of horizontal or vertical movement of the probe 1 on the object 2 to a linear potentiometer 403 for detecting the amount of horizontal movement or to a linear potentiometer 404 for detecting the amount of vertical movement. The pantograph 402 is connected through a supporting point 405 on the pantograph to the support 401 extendibly. The outputs from the linear type potentiometers 403 and 404 are applied as the $X_O$ and $Y_O$ inputs to adders 419 and 416 shown in FIG. 8, as will be described later.

An embodiment of the circuit device for generating the X and Y sweep signals required for displaying the scanning lines O1-R1-P1 on the display screen 4 of FIG. 2 in accordance with the transmission path of the supersonic wave beam will be explained with reference to FIGS. 6 to 8 below.

Referring to FIG. 6 showing a block diagram of the sector scanning type supersonic wave flaw detecting apparatus according to an embodiment of the invention, reference numeral 1 shows a variable angle beam probe having a driving mechanism for sector scanning, numeral 2 an object to be inspected, and numeral 6 an angle/position detector having a mechanism for detecting the incident angle $\theta$ of the supersonic wave beam entering the object 2 or the angle and position for the sector scanning along the surface 201 of the object 2. The angle stored in the angle/position detector 6 is detected by the potentiometer 306 in FIG. 3a. The position stored in the angle/position detector, on the other hand, is detected by the potentiometers 403 and 404 in FIG. 4. Numeral 7 shows a supersonic wave transmitter/receiver such as Branson 600. Numeral 8 shows a scanning signal generator for generating the X and Y deflection signals for forming the display scanning lines on the screen of the displaying device 212. Numeral 9 shows a synchronizing signal generator for determining the repetition frequency of the supersonic wave pulses delivered from the supersonic wave transmitter/receiver 7 and at the same time triggering the deflection signals generated by the scanning signal generator 8. The synchronizing signal generator 9 may consist of Tektronix PG501 pulse generator or Tektronix 140 NTSC signal generator. Numeral 10 shows a scanning mode control device for switching the scanning mode of sectorial display in response to the angular signal from the angle/position detector 6. Numeral 11 shows an image signal memory unit for storing a sectional display image, which may consist of PEP-400 VIDEO/GRAPHIC STORAGE TERMINAL of Princeton Electronic Products, Inc. Numeral 212 shows a displaying device for displaying a sectional display image.

The operation of the foregoing embodiment will be explained below. When the variable angle beam probe 1 performs the sector scanning or compound scanning, the angle for sector scanning and the amount of horizontal and vertical movement of the probe are produced from the angle/position detector 6 in the form of the outputs from the potentiometers 306 and 403 and 404 as described already. After the angle/position detector 6 detects the angle of sector scanning $\theta$ and the position X of the object along the surface 201 thereof, a signal (E $\theta$) associated with the angle $\theta$ is applied from the angle/position detector 6 to the scanning mode control device 10. In the range of $\theta$ from 0° to 19° (the incident angle corresponding to $\alpha_1$ in FIG. 5), the scanning mode control device 10 applies to the scanning signal generator 8 a command signal for generating a display scanning signal of the longitudinal wave mode; In the range of $\theta$ from 19° (the incident angle corresponding to $\alpha_1$ in FIG. 5) to 36° (the incident angle corresponding to $\alpha_2$ in FIG. 5 as mentioned earlier), it delivers a command signal for ceasing the display scanning to the scanning signal generator 8; and in the range of $\theta$ from 36° (the incident angle corresponding to $\alpha_2$ in FIG. 5) to 62° (the incident angle corresponding to $\alpha_3$ in FIG. 5), it sends to the scanning signal generator 8 a command signal for generating a display scanning signal in the shear wave mode. In this case, the sectional image display section comprising the image signal memory unit 11 and the displaying device such as a CRT display unit 212, as will be understood from FIGS. 2 and 5, displays a single collective sectional image including the flaw image 203' detected by the longitudinal wave in FIG. 2 in the range from 0° to 45° of the refraction angle in the object 2 in FIG. 5 and the flaw image 202' detected by the shear wave in FIG. 2 in the range from 45° to 90° in FIG. 5. In short, the object of inspection covering the complete range of angles is searched for flaws.

The construction and operation of the scanning mode control device 10 of FIG. 6, an example of which is shown in the block diagram of FIG. 7a, will be explained. Reference numerals 1001, 1002, 1003, 1001', 1002' and 1003' show reference generators. The above-mentioned angle $\alpha_1$ in FIG. 5 defining the upper limit of the range of scanning by longitudinal wave mode is set at the reference generator 1001. The angle $-\alpha_1$ is set at the reference generator 1001'. The above-mentioned angle $\alpha_2$ of FIG. 5 representing the lower limit of the range of scanning by shear wave is set at the generator 1002. Angle $-\alpha_2$ is set at the generator 1002'. The upper limit angle $\alpha_3$ in FIG. 5 is set at the generator 1003. Angle $-\alpha_3$ is set at the generator 1003'. The outputs of these reference generators are applied to the comparators 1004, 1005, 1006, 1004', 1005' and 1006' respectively and compared therein with the signal E $\theta$ associated with the incident angle $\theta$. An output signal in the state of +1 is produced in the range of longitudinal wave mode scanning satisfying the relation $\alpha_1 \geq \theta \geq 0$, while an output signal in the state of O is produced in the range $\alpha_1 < \theta$, by the comparator 1004. The comparator 1005 produces a O signal in the range $\alpha_2 > \theta$, and +1 signal in the shear wave mode scanning range satisfying the relation $\alpha_2 \leq \theta \leq \alpha_3$. The comparator 1006 produces an output signal in the state of O in the range satisfying the relation $\alpha_3 < \theta$. In like manner, the comparator 1004′ produces a +1 signal in the range $-\alpha_1 \geq \theta$; the comparator 1005′ produces a O signal in the range $a_2 < \theta$; and the comparator 1006′ produces O signal in the range satisfying the relation $a_3 < \theta$. The logic circuit 1007 produces a control output signal $C_1$ or $C_2$ in the state of +1 when $|\pm\alpha_1| > |\theta|$, in the state of O when $|\pm\alpha_1| < |\theta| < |\pm\alpha_2 \alpha|$ in the state of 0 when $|\theta| < |\pm\alpha_2|$, in the state of +1 when $|\pm\alpha_2| < |\theta| < |\pm\alpha_3|$ and in the state of 0 when $|\pm\alpha_3| < |\theta|$. These control output signals are applied to the scanning signal generator circuit 8. The signal $C_1$ or $C_2$ for effecting the scanning by longitudinal wave mode, cease of the longitudinal wave mode scanning, scanning by shear wave mode and cease of the shear wave mode scanning are produced from the scanning signal generator 8 and applied to the sectional image display section in accordance with the values of +1, 0, −1 and 0. Instead of producing the output signal $C_1$ or $C_2$ from the scanning mode control device in accordance with the values of the sector scanning angle $\theta$ as explained with reference to FIG. 7a, the output signal $C_1$ or $C_2$ corresponding to the input of either $+|\theta|$ or $|\theta|$ may be produced. Alternatively, the output passed through an absolute value circuit 1030 provided at the input terminal section of the scanning mode control device 10 as shown in FIG. 7b is appropriately processed so that the scanning mode control device may produce the output $C_1$ or $C_2$. As another possibility, the circuit energized when the scanning angle $\theta$ exceeds $|\pm\alpha_3|$ may be omitted as required. By the way, the above-mentioned logic circuit 1007 may be easily constructed by a combination of, say, Texas 74-series. Further, the values of outputs $C_1 C_2$ from the logic circuit 1007 corresponding to the incident angle or scanning angle $\theta$ are shown in FIG. 7c.

Next, a circuit device for generating X and Y sweep signals required for displaying the scanning lines O1-R1-P1 associated with the transmission path of supersonic wave beam on the display section 12 as shown in FIG. 2 will be explained with reference to an embodiment thereof shown in FIG. 8. In the drawing under consideration, the portion surrounded by two-dot chain lines and numerals denote like component parts shown in FIG. 6.

Reference numeral 101 shows the transducer for transmitting and receiving supersonic waves which is mounted on the variable angle beam probe, numeral 2 an object to be inspected, numeral 401 a trigger pulse generator for generating trigger pulses at a predetermined frequency serving as a sync signal as from the sync signal generator 9 (FIG. 6), and numeral 402 a pulse oscillation circuit for generating a pulse output and applying supersonic waves to the transducer 101 in response to the trigger pulse from the pulse generator 401. Numeral 403 shows an amplifier for amplifying the supersonic wave signal received by the transducer 101, and numeral 404 a brightness modulator circuit for applying a brightness-modulated signal to the display section 212 of the CRT of, say, storage type in response to the output from the amplifier 403. Numeral 405 shows a saw-tooth wave generator circuit which produces a saw-tooth wave $V_1 t$ having a gradient corresponding to the sound velocity $V_1$ in the supersonic wave transmission medium with the receipt of the output pulse from the generator circuit 401 as a starting point. The output signal in the form of saw-tooth wave $V_1 t$ is then applied to the delay circuit 406.

On the other hand, the voltage $E \theta$ associated with the direction angle $\theta$ obtained from the potentiometer 306 mounted on the variable angle beam probe 300 is converted into signals of $\sin\theta$ and $\cos\theta$ by the sin·cos modulator 407. Of these output signals, the $\cos\theta$ signal is converted into a $2d/\cos\theta$ signal by the divider 408. This last-mentioned signal is compared with the saw-tooth wave signal $V_1 t$ in the delay circuit 406, thus producing a delay pulse representing the delay time $t'R$. The saw-tooth wave generator circuit $409_1$ having a gradient corresponding to the velocity of the shear wave and the saw-tooth wave generator $409_2$ having a gradient corresponding to the velocity of the longitudinal wave generate saw-tooth wave signals $V_s/2 (t-t'R)$ and $Vl/2 (t-t'R)$ respectively having gradients of $V_s/2$ and $V_t/2$ ($V_s$ corresponding to the velocity of shear wave and $V_t$ to the velocity of longitudinal wave) with the delay pulse as a starting point. It should be noted, however, that $V_s/2 (t-t'_R)$ and $V_l/2 (t-t'_R)$ are combined in the representative form of $V_l/2 (t-t'_R)$ in FIG. 8. The saw-tooth wave generated in the saw-tooth wave generator circuits $409_1$ and $409_2$ are switched in the analog switch 430 by the signals from $C_1$ or $C_2$ shown in FIG. 7a or FIG. 7b. As a result, the signals $V_l/2 (t-t'_R)$ and $V_s/2 (t-t'_R)$ are applied to the multipliers 410 and 411 respectively when the signals $C_1$ and $C_2$ are high respectively.

The output $\sin\theta$ from the sin·cos modulator 407 is converted into signals $n_1·\sin\theta$ and $n_2·\sin\theta$ by the coefficient multiplier $412_1$ related to the refraction factor $n_1$ for longitudinal wave and the coefficient multiplier $412_2$ related to the refraction factor $n_2$ for shear wave, respectively. The outputs from the coefficient multipliers $412_1$ and $412_2$ are applied to the analog switch 431, where they are switched by the signal $C_1$ or $C_2$ from FIG. 7a or FIG. 7b thereby to produce the signal $n_1·\sin\theta$ or $n_2·\sin\theta$. In the process, the signal $n_1·\sin\theta$ is produced from the analog switch 431 when the value of signal $C_1$ is high, whereas the signal $n_2·\sin\theta$ is generated when $C_2$ is high. In this connection, a representative signal $n·\sin\theta$ combining the signals $n_1·\sin\theta$ and $n_2·\sin\theta$ is shown in FIG. 8.

The signal produced from the analog switch 431 is subjected to calculating processes in the squarer 413, divider 414 and rooter 415 and converted into the signal expressed by $\sqrt{1-n^2·\sin^2\theta}$. This signal is multiplied by the above-mentioned signal $V_2/s (t-t'_R)$ in the multiplier 411 and takes form of the signal output $V_2/2 \sqrt{1-n^2·\sin^2\theta}(t-t'_R)$. This signal is added to the signal $d$ associated with distance from the transducer 301 to the surface 141 of the inspection object and also to the signal representative of the position $y_0$ of the probe 300 in Y direction which is obtained from the vertical linear type potentiometer 404. As a result, the Y deflection signal $E_y$ is obtained for the display section 212.

On the other hand, the signal $V_2/2 (t-t'_R)$ and the signal $n·\sin\theta$ obtained from the coefficient multiplier 412 are multiplied in the multiplier 410, which produces the signal $n·V_2/2 \sin\theta (t-t'_R)$ and applies it to the adder 419. Reference numeral 417 shows a divider which divides the signal $\sin\theta$ by signal $\cos\theta$ thereby to produce signal $\tan\theta$, which is converted into signal $d·\tan\theta$ by the coefficient multiplier 418 and applied to the adder 419. The signals obtained from the multiplier 410 and the coefficient multiplier 418 are added in the adder 419 to the signal representative of the position $x_0$ of the probe 300 in X direction which is obtained from the horizontal linear potentiometer 403, so that the X deflection signal $E_x$ for the display section 212 is produced from the adder 419.

The X and Y sweeping on the display device 212 is performed by the use of deflection signals $E_x$ and $E_y$, while effecting the brightness modulation by the supersonic wave image signal obtained from the brightness modulator circuit 404. In this way, a supersonic wave sectional image is displayed.

The scanning signal generator 8 may roughly be divided into the parts (A), (B) and (C) defined below, as illustrated by dotted lines in FIG. 8. A. Means for calculating the time required for the supersonic wave beam starting at the variable angle probe to reach and return from the incident point on the inspection object. B. Means for switching and generating the output signals related to the refraction of the longitudinal wave and shear wave of the supersonic wave entering the inspection object of the incident point, by the use of the signal obtained from the scanning mode control device. C. Means for generating the display scanning signal for the display unit in accordance with the transmission speed of the longitudinal and shear waves in response to the output signals from the return time-calculating means and the output signal generator means mentioned in (B) above.

Figure 8:
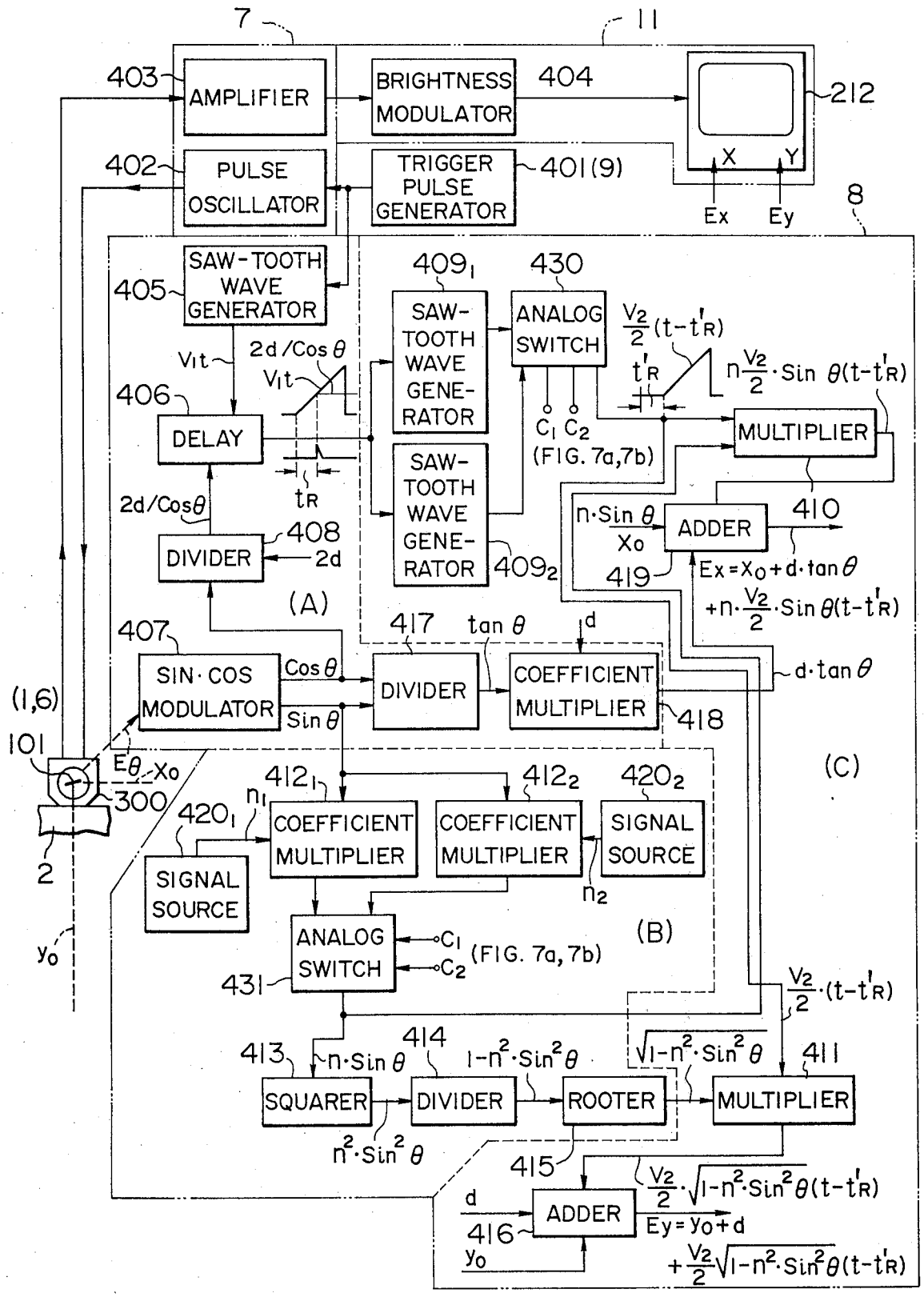
FIG. 8 is a diagram showing the circuit of FIG. 6 more in detail.
Figure 9:
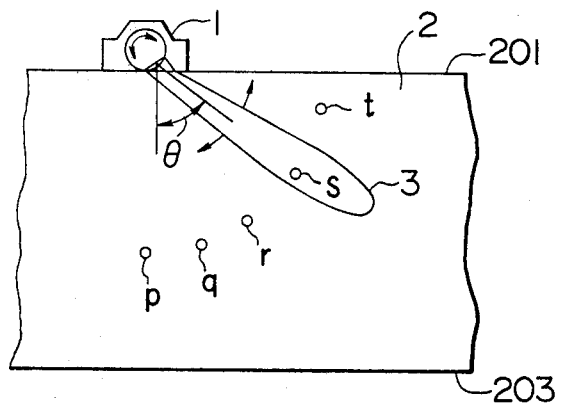
FIG. 9 is a diagram for explaining an example of supersonic wave flaw detection by the sector scanning.
Figure 10:
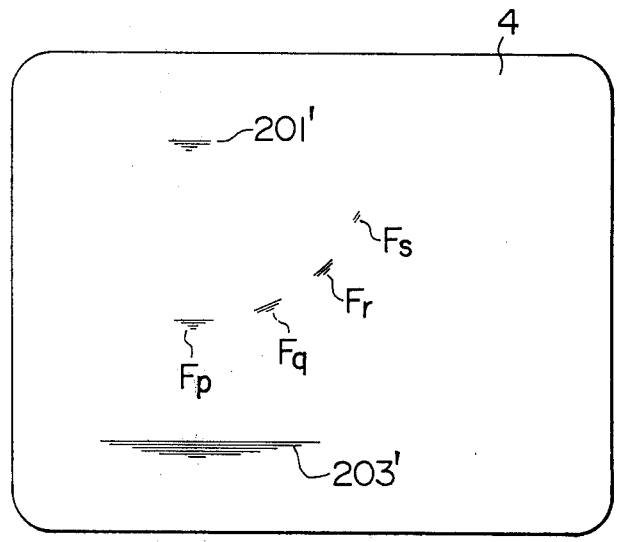
FIG. 10 shows an example of a section displayed by the conventional method and device using only a longitudinal wave for supersonic wave flaw detection.

The circuit configuration as shown by the embodiment of FIG. 8 permits a high sensitivity of flaw detection to be obtained over the whole angular range of sector scanning by the variable angle beam probe 1. Suppose there are flaws $p$, $q$, $r$, $s$, and $t$ or foreign matters in the object as shown in FIG. 9. In the conventional supersonic wave detector device using only the longitudinal wave, the flaws A, B and C which are capable of being detected at comparatively small angles of incidence $\theta$ as shown in FIG. 10 are displayed as $F_p$, $F_q$ and $F_r$ on the sectional image on the display screen 4. It is, however, impossible to detect the flaw s or t which involves a large incident angle $\theta$ and hence reduced flaw detection sensitivity.

Figure 11:
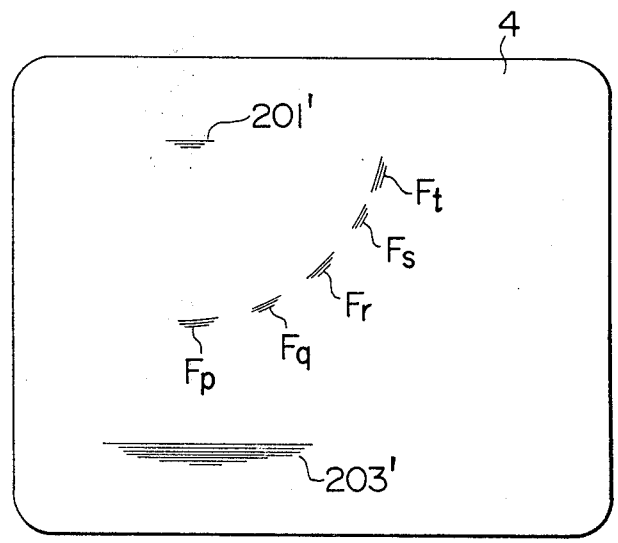
FIG. 11 is a diagram showing an example of a sectional area displayed by the present invention.

According to the present invention, however, the longitudinal wave is used in the range of small incident angle $\theta$, whereas the shear wave is utilized and therefore the flaw detection sensitivity is not reduced for the flaws $s$ and $t$ requiring a larger incident angle $\theta$. The diagram of FIG. 11 shows the sectional image displayed on the display screen 4 in the above-mentioned case. As will be noted, the sectional image of all the flaws $p$, $q$, $r$, $s$ and $t$ are displayed as $F_p$, $F_q$, $F_r$, $F_s$ and $F_t$, thereby making possible accurate flaw detection.

In place of the image memory unit 11 and recording device 12 making up the B scope image display section used in the construction of FIG. 8, the image of a flaw detected may be more simply displayed by the use of a storage type of CRT device.

Figure 7B:
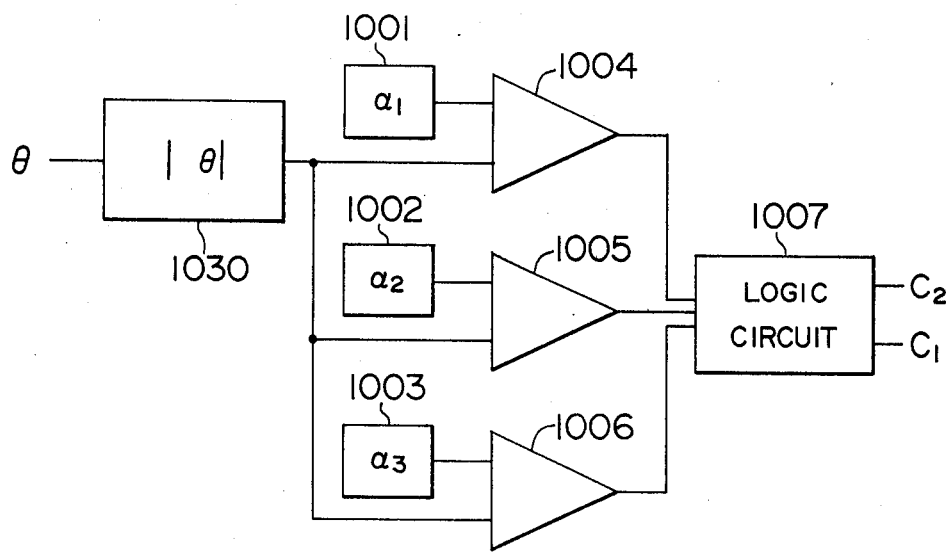
Figure 7C:
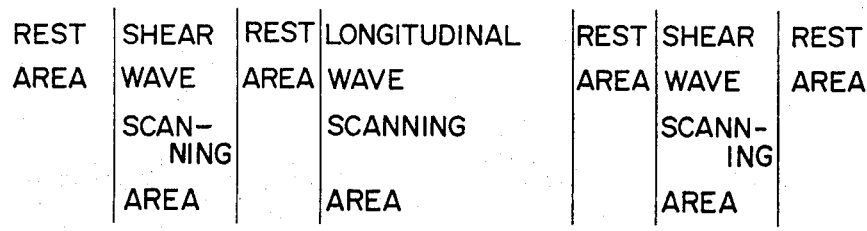
FIG. 7c is a diagram for explaining the operation of the circuits shown in FIGS. 7a and 7b.

Further, the embodiments of FIGS. 7a and 7b are such that the outputs $C_1$ and $C_2$ from the logic circuit 1007 are zero in the range of $\pm\alpha_3 < \theta$ as shown in FIG. 7c, and therefore the signal which otherwise is transmitted from the analog switches 430 and 431 to the subsequent stages including the display device 212 in FIG. 8 is cut off, thus preventing noise signals from being displayed on the display screen 4.

Figure 12:
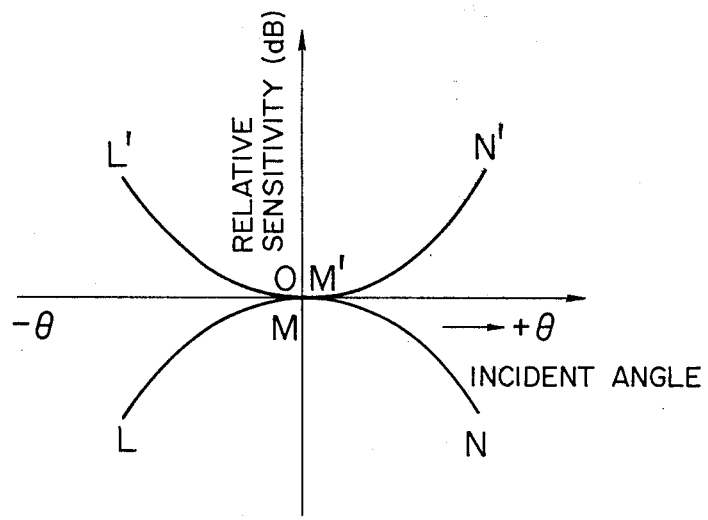
FIG. 12 is a diagram for explaining the effect of the incident angle on the efficiency of incidence of the supersonic wave into the object and its compensation characteristics.

Now, in effecting the sector scanning by the supersonic wave beam, a problem is posed in which the transmission factor of supersonic wave in the object of inspection changes with the incident angle, thus subjecting the flaw detection sensitivity to variations. An embodiment of the present invention to solve such a problem will be explained below with reference to FIG. 12.

The drawing under consideration shows that the flaw detection sensitivity of the apparatus using the variable angle beam probe shown in FIG. 3 changes with the direction angle $\theta$ of the vibration element, as will be apparent from the curve LMN. In order to compensate for this characteristic, the gain of the supersonic wave echo signal amplifier is controlled as relative to the angle $\theta$ by the angular signal E $\theta$ in such a manner as to attain the characteristic curve L'M'N'. In this way, the flaw detection sensitivity may be maintained uniform in spite of the change in the direction angle $\theta$.

Figure 13:
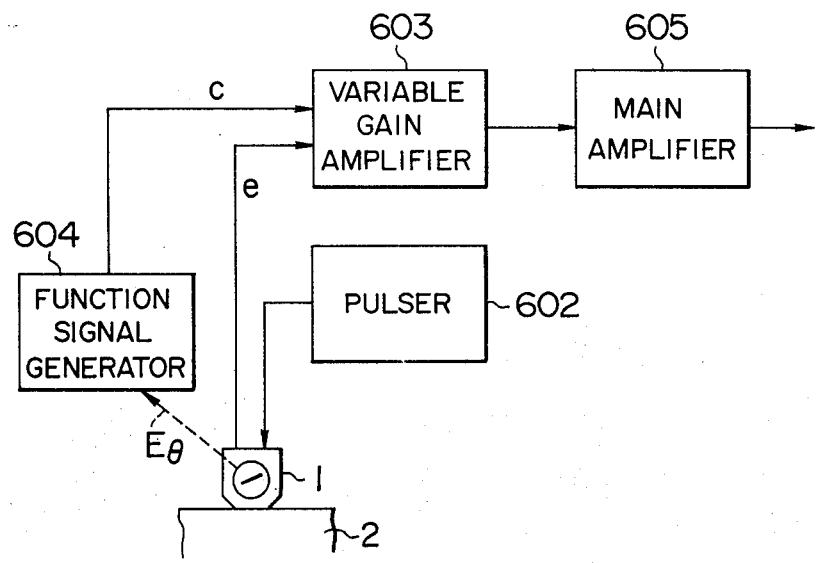
FIG. 13 is a diagram showing another embodiment of the present invention.

An embodiment of the invention for performing such a signal control is shown in the circuit block diagram of FIG. 13. In this drawing, reference numeral 1 shows a variable angle beam probe capable of generating the angular signal E $\theta$ associated with the angle $\theta$ of direction of transmission and receipt of the supersonic wave as described with reference to FIG. 3, numeral 602 a pulser for generating supersonic wave pulses upon pulse excitation of the probe 1, numeral 603 a variable gain amplifier for amplifying the signal $e$ received by the probe 1 and having an amplification gain capable of being controlled by an external control signal $c$, numeral 604 a function signal generator for generating the control signal C for attaining such a gain for the variable gain amplifier 603 as relative to the angle $\theta$ as to obtain the characteristic curve L'M'N' in response to the angular signal E$\theta$, and numeral 605 a main amplifier. By using the above-mentioned circuit arrangement, a supersonic wave flaw detecting operation with uniform sensitivity characteristics can be performed independently of the direction of the probe, that is, the incident angles of the supersonic wave beam.

As will be understood from the foregoing description, in performing the supersonic wave flaw detecting operation by the sector scanning of a supersonic wave beam using the variable angle beam probe according to the invention, the longitudinal and shear waves are utilized at comparatively small and large incident angles respectively. As a result, a high flaw detection sensitivity is attained over the entire range of angles of sector scanning and the sectional images due to both longitudinal and shear waves are displayed on a single display screen.

We claim:

1. A supersonic wave flaw detecting apparatus comprising a variable angle beam probe for performing sector scanning by transmitting and receiving a supersonic wave beam while maintaining acoustic contact with an object of inspection, said probe generating an electrical signal in accordance with the direction of transmission and receiving of the supersonic wave beam, a display unit for displaying an acoustic sectional image of said object on a display screen of said display unit, said display unit brightness-modulating the display scanning lines with an echo signal of said supersonic wave beam received from said object by said variable angle beam probe, said display scanning lines being associated with the transmission path and transmission velocity of said supersonic wave beam in said object of inspection, an angle detector for detecting the incident angle of said supersonic wave beam from said variable angle beam probe and generating an angular signal, a scanning mode control device for generating command signals in accordance with the two modes of the longitudinal wave and shear wave in response to the angular signal from said angle detector, and a scanning signal generator for producing a display scanning signal for said display unit in accordance with the velocity and direction of transmission of a selected one of the longitudinal wave and shear wave of the supersonic wave beam in response to said command signals produced from said scanning mode control device and said angular signal produced from said angle detector.

2. A supersonic wave flaw detecting apparatus according to claim 1, in which said variable angle beam probe comprises means capable of performing sector scanning and compound scanning which is a combination of sector scanning and shift scanning, said angle detector further comprises position detector means for detecting the position of said variable angle beam probe, and said scanning signal generator further comprises means for generating said display scanning signal for said display unit in response to said signal from said scanning mode control device, said signal from said angle detector and a position signal from said position detector.

3. A supersonic wave flaw detecting apparatus according to claim 2, in which said position detector comprises mechanical means actuated in direct response to the horizontal and vertical movement of said variable angle beam probe, and a device for converting the output of said mechanical means into an electrical signal.

4. A supersonic wave flaw detecting apparatus according to claim 1, in which said angle detector produces an angular signal associated with a selected one of positive and negative rotational angles of said variable angle beam probe.

5. A supersonic wave flaw detecting apparatus according to claim 1, in which said scanning mode control device receiving a selected one of positive and negative angular signals from said angle detector comprises at least one device for setting a selected one of positive and negative reference values, and at least one comparator for comparing an output signal from said reference device with the signal from said angle detector, said comparator producing outputs of different values when said signal from said angle detector is larger than, smaller than and equal to said reference values set by the reference device.

6. A supersonic wave flaw detecting apparatus according to claim 5, in which said reference value setting device is constructed in such a manner that said comparator produces output signals associated with the upper and lower limits of the range of angles for detection of flaws by the longitudinal wave and shear wave.

7. A supersonic wave flaw detecting apparatus according to claim 1, in which said scanning signal generator comprises means for calculating in response to said electrical signal the time required for said supersonic wave beam to cover the distance from said variable angle beam probe to said incident point on said object and return to said variable angle beam probe, means for generating and switching an output signal representative of the refraction of the longitudinal wave and shear wave of the supersonic wave beam entering said object by way of said incident point, in response to said signal from said scanning mode control device, and means for generating a display scanning signal for said display unit in accordance with the transmission velocity of said longitudinal wave and said shear wave in response to said output signals from said return time calculating means and said signal-switching/generating means.

8. A supersonic wave flaw detecting apparatus according to claim 7, in which said scanning signal generator produces an output signal by adding the amount of a selected one of horizontal and vertical movements which is applied to said angle detector from said position detector.

9. A supersonic wave flaw detecting apparatus according to claim 7, in which said return time calculating means comprises means for calculating the distance from transmitter-receiver of said variable angle beam probe to the incident point on the basis of the normal distance $d$ from said transmitter-receiver of said variable angle beam probe to said object of inspection and the scanning angle of the supersonic wave beam emitted from said variable angle beam probe, means for producing an output corresponding to the sound velocity $V_1$ in the medium receiving the supersonic wave, multiplied by time $t$ required for supersonic wave beam to pass said medium, said medium being maintained in acoustic contact with said object, said time $t$ being a variable, and another means for generating an output by delaying said output from said first generating means by the time equivalent to twice the time $t$ corresponding to said distance from said transmitter-receiver to said incident point.

10. A supersonic wave flaw detecting apparatus according to claim 9, in which said means for generating the display scanning line for said display unit comprises: first calculating means for calculating the Y components of the distances from said transmitter-receiver to each point of the transmission path of said supersonic wave on the basis of said values $d$ and $\theta$ and the refraction factor $N_1$ of longitudinal wave, refraction factor $N_2$ of shear wave, sound velocity $V_{2l}$ of longitudinal wave in said object, and sound velocity $V_{2s}$ of shear wave in said object, the result of said calculation being superimposed on the output of said means for generating the position signal for said probe and applying said position signal to said display unit, the result of said superimposition being applied as a Y input to said display unit; and second calculating means for calculating the X components of the distances from said transmitter-receiver to each point of the transmission path of said supersonic wave on the basis of said values $d$, $\theta$, $N_1$, $N_2$, $V_{2l}$, and $V_{2s}$, the result of said calculation being superimposed on the output of said means for generating the position signal for said probe and applying said position signal to said display unit, the result of said superimposition being applied as an X input to said display unit.

11. A supersonic wave flaw detecting apparatus according to claim 1, in which said angle detector includes mechanical means actuated in direct response to the rotation of said variable angle beam probe and a device for converting the output of said mechanical means into an electrical output signal.

12. A supersonic wave flaw detecting apparatus according to claim 1, further comprising means for controlling the signal received by said variable angle beam probe, in accordance with the variation of the scanning angle $\theta$ of the supersonic wave beam emitted from said variable angle beam probe.

13. A supersonic wave flaw detecting apparatus according to claim 1, in which said variable angle beam probe comprises a movable section for sectorial motion having a transducer for transmission and receiving of supersonic wave, a holding section for supporting said movable section and holding said acoustic contact of said variable angle beam probe with said object of inspection, and means for generating and electrical signal representative of the rotational angle of said variable angle beam probe for sectorial motion.

* * * * *